United States Patent [19]

Walker et al.

[11] Patent Number: 4,822,365
[45] Date of Patent: Apr. 18, 1989

[54] METHOD OF DESIGN OF HUMAN JOINT PROSTHESIS

[76] Inventors: Peter S. Walker, 15 Hallette Hill Rd.; Frederick C. Ewald, 4 Black Oak Rd., both of Weston, Mass. 02193

[21] Appl. No.: 97,286

[22] Filed: Sep. 11, 1987

Related U.S. Application Data

[63] Continuation-in-part of Ser. No. 868,609, May 30, 1986, abandoned.

[51] Int. Cl.$^4$ .......................... A61F 2/38; B23Q 15/14
[52] U.S. Cl. ......................................... 623/20; 623/66; 364/468
[58] Field of Search ............................ 623/18, 20–23, 623/66; 364/468, 474, 475, 512

[56] References Cited

U.S. PATENT DOCUMENTS

| | | | |
|---|---|---|---|
| 3,945,053 | 3/1976 | Hillberry et al. | 623/20 |
| 4,470,158 | 9/1984 | Pappas et al. | 623/20 |
| 4,611,288 | 9/1986 | Duret et al. | 364/474 |
| 4,634,444 | 1/1987 | Noiles | 623/20 |
| 4,663,720 | 5/1987 | Duret et al. | 364/474 |
| 4,704,686 | 11/1987 | Aldinger | 364/468 |

Primary Examiner—Richard J. Apley
Assistant Examiner—Alan W. Cannon
Attorney, Agent, or Firm—Wolf, Greenfield & Sacks

[57] ABSTRACT

A method of designing a prosthesis having convex male and concave female mating portions is provided for a human joint comprising a condylar male portion the surface of which is generated by the piecewise analysis of an anatomical condyle, which can be an average condyle or a selected condyle, or a distortion of an average condyle to fit the observed general dimensions of a specific patient, and the female portion having at least flexion and laxity surfaces, the flexion surfaces of which are generated by plotting the path of articulation of substantial points of contact between said male portion and a corresponding anatomical female component for said joint through the full normal extension-flexion range plus normal rotation and posterior-anterior displacement for that joint, and the laxity surfaces of said female member comprising raised guide-bearing surfaces for resisting dislocation of the condylar portion, the height and angle, and therefore, the resistance to dislocation, of which guide bearing surfaces increases as a function of deviation from the central motion path of said male portion and as a function of the flexion angle, and which at full laxity for any given angle of flexion corresponds substantially to the forces of anatomical ligamentous restraint of said anatomical joint at the limits of laxity.

3 Claims, 7 Drawing Sheets

METHOD OF DESIGN OF HUMAN JOINT PROSTHESIS

The present application is a continuation in part of application Ser. No. 868,609, filed on May 30, 1986 by the same inventors, now abandoned.

BACKGROUND OF THE INVENTION

The present invention relates prostheses for human joints, and more particularly to prostheses for knee, elbow, or other joints of the body, and more particularly to a method for designing the same. In particular, the present invention has a preferred application as a knee prosthesis. The movement of the knee joint in flexion and extension does not take place in a simple hinge-like manner, as in some other joints, but in a complicated movement, that includes displacements and rotations, so that the same part of one articular surface is not always applied to the same part of the other articular surface, and the axis of motion is not fixed. Furthermore, the knee joint is formed between the longest bones of the body, consequently with high lever arms relative to the foot and to the hip, and therefore, the forces and moments across the joint at the interface between the articulating surfaces exceeds that of any other joint in the body.

Attempts to implant knee prostheses employing a metal hinge and intramedullary stems for anchoring the hinge to the femur and tibia date back to the 1930's. Because of the complexity of the knee joint action, and the forces and moments across the joint, these prostheses were unsuccessful. The elements were subject to wear resulting in dispersion of metal into the surrounding tissue with consequent complications, and in high stresses at the implant-bone interfaces resulting in bone resorption, pain, and implant failure. However, a hinge does not permit ready access of natural lubrication to the joint, and, by its nature, permits rotation only through a single plane. It cannot duplicate the complex movements of the knee joint. Thus, a less than satisfactory result is inevitable. See, e.g., D. V. Girzadas et al., "Performance of a Hinged Metal Knee Prosthesis", J. Bone and Joint Surgery, Vol. 50-A, No. 2, March 1968, pp. 355 et seq.

Since that time, unlinked condylar replacement knee replacements have been designed. These allowed some freedom of motion between the femoral and tibial replacement surfaces. The first example was the polycentric knee by Gunston. (Gunston, J. Bone & Joint Surgery)

Another early design was by Ewald, in which he proposed surfaces representing the anatomical to allow normal joint motion. The Ewald prosthesis was an advancement over the earlier knees in that it permits rotation of the tibia with respect to the femur (i.e., pivoting of the medial condyle about the lateral condyle), and translation of the femur with respect to the tibia-movements in different planes at once (sagittal and transverse). All of those movements are necessary to duplicate the movement of a natural knee. For a detailed description of the control mechanism and the guiding components of the knee joint during normal extension and more particularly flexion, see O. C. Brantigan et al., "The Mechanics of the Ligaments and Menisci of the Knee Joint", J. Bone and Joint Surgery, Vol. XXIII, No. 1, January 1941, pp. 44 et seq.; and A. J. Helfet, "Control and Guide Mechanism of the Knee Joint", A.A.O.S. Instructional Course Lectures (1970), pp. 64–65.

However, although the Ewald prosthesis provided a more natural movement than the prior art knee joints, the Ewald knee was not designed to allow for the natural knee movement known as laxity. Laxity can be defined as the partially restrained motion or free play in a specified direction before substantial ligamentous restraint takes place at the extremes of motion (see generally, Markolf, K. L., et al, Journal of Bone & Joint Surgery, 63-A; 570–585, 1981; Walker, P. S. Ch. 4, p. 202-204, Human Joints & Their Artificial Replacements, pub. C. C. Thomas, Springfield, Ill., 1977). Since laxity is limited by certain ligaments that are resected during implantation of a prosthesis, primarily the cruciate ligaments, prior to the present invention, there was a need in the art for a prosthesis capable of duplicating the laxity characteristics of a natural knee joint.

Several designs allowed freedom of motion, by providing partial conformity between the femoral and tibial surfaces, using geometrical radii of curvature. These designs included the DuoPatella, Townley, Total Condylar, and Anametric. However, the shape of the surfaces is not related to the actual motion and laxity of the normal knee joint.

The femoral condyles of a knee prosthesis can be joined to the femur in several different ways. One method is to provide two pegs which insert into the trabecular bone of the medial and lateral femoral condyles. Another method is to provide a stem that projects from the center of the condyles and is inserted into and locked within the medullary canal of the femur. Because of the valgus angle of the femur, it was necessary to provide both right and left femoral components, which were not interchangeable with each other. In addition, certain situations require a short stem, while others require a long stem. Thus, it was necessary to maintain in stock four different femoral components—long stem and short stem versions of both left and right leg components.

OBJECTS AND SUMMARY OF THE PRESENT INVENTION

It is therefore, a general object of this invention, to provide a method of designing a prosthesis which overcomes the foregoing limitations of the known prostheses.

A more specific object of the invention is to provide a method of designing a prosthesis that provides joint motion which accurately simulates the motion of the natural joint.

It is a further object of the invention to provide a method of designing a prosthesis that accounts for laxity in the motion of the joint.

It is yet a further object of the invention to provide a knee joint prosthesis that facilitates walking, stair climbing, stair descending, rising from a chair, and other uses of the joint.

It is still a further object of the present invention to provide a prosthesis that facilitates the access of the natural lubricating synovial fluid to the mating surfaces and escape of wear and other abrasive particles within and around the prosthesis.

Yet another object of the present invention is to provide a prosthesis which acts cooperatively with the natural ligaments remaining after the surgery to cause the respective components of the prosthesis to move substantially as in nature including flexion-extension, varus-valgus, internal-external rotation, anterior-posterior displacement, and laxity.

Briefly described, the joint prosthesis made by the process of the present invention includes a substantially smooth male portion and a mating female portion designed to interact. In general, the male portion is similar in shape and size to the end of the bone which it replaces, as determined by sectioning measurements of a plurality of actual specimens.

The female portion is considerably different in shape from the natural female member since it includes articular surfaces which are shaped to provide the required stability, motion and laxity, previously provided by structures such as menisci and ligaments, which are necessarily resected at surgery or are made ineffective by the disease. In other joints such as the elbow, etc., the articular surfaces of the prosthesis likewise function as the capsular or the like ligaments which may have been destroyed by disease or injury, or necessarily resected during prosthetic replacement.

The knee prosthesis of the present invention comprises in combination two components: a femoral component and a tibial plateau. These components are mated, preferably by the method herein described, so that they operate in conjunction to permit normal knee-joint functioning. In particular, the tibial plateau comprises articular surfaces, described in greater detail hereinafter, which operate in conjunction with the femoral component, to accomplish substantially the same result as the combination of the tibial surfaces, the collateral and cruciate ligaments, and menisci in the natural knee.

The femoral component may comprise a pair of condyles and is similar in size and shape to the distal end of a normal average femur, and has a range of sizes to span the normal size ranges of human knee joints. A model for the femoral component may be imagined by cutting the articular surfaces from the outer surfaces of an anatomical distal femur, while forming medial and lateral condyles, substantially smooth and rounded in shape.

A particular improvement of one form of the present invention over the prior art knee joint prostheses is that the femoral component bearing geometry is a piecewise mathematical analog of the average anatomical femoral surface geometry, with a range of sizes.

The tibial plateau component of the method of the present invention is considerably different from the proximal end of a normal tibia. Part of the reason for this difference is the objective that the component, in conjunction with the ligaments remaining after surgical intervention and the femoral component, perform the function of the cruciate ligaments and the menisci in the normal knee joint. Thus, the tibial plateau includes means to provide for the appropriate amount of stability, guide the joint surfaces in an anatomical motion path, but allow for normal laxity, as the knee moves in its full flexion-extension range. Such means may include means to guide the lateral condyle of the femoral component during flexion in a substantially anterior-posterior direction through a curved articular surface of the tibial plateau while rotating and translating the femur-tibia in the sagittal plane. These means may be provided by extension surfaces in the tibial plateau mated at extension with the condyles of the femoral component with maximal surface contact, flexion surfaces mated during flexion with the condyles with substantial surface contact, and raised extending upwardly curved guiding-bearing laxity surfaces for guiding the movement during flexion and resisting dislocation gradually but increasingly as respective components depart from the desired path.

The tibial plateau component is created from a computer generated design originated by sweeping the femoral bearing surface through the prescribed motion, including three displacements and two rotations defined as a function of flexion in polynomial equations, with laxity superimposed. The superimposed laxity consists of anterior-posterior displacement, medial-lateral displacement, and internal-external rotation. The laxity curves are polynomial equations describing increasing resistance as a function of deviation from the central motion path, and as a function of flexion angle.

These and other objects, advantages and features of the invention will be more clearly understood by reference to the following detailed description thereof, the appended claims, and to the several views illustrated in the attached drawings.

BRIEF DESCRIPTION OF THE DRAWINGS

The present invention will be better understood by reference to the attached drawings, which illustrate the present invention, and wherein.

DETAILED DESCRIPTION OF THE INVENTION

The present invention is directed to a method for designing joint prosthesis comprising a male portion and a mated female portion having articular surfaces for mating with the male portion in the full range of positions of joint flexion. The female portion preferably has flexion surfaces for mating throughout the joint movement during flexion, as well as raised guiding-bearing surfaces to guide the joint through flexion and to resist dislocation, thereby performing or supplementing the functions of collateral or cruciate ligaments, and, depending on the joint function, optionally an extension surface for mating with the male portion at extension.

An important aspect of the present invention is that the femoral and tibial components are totally designed by computer programs.

The invention in a preferred embodiment comprises a method for designing a knee prosthesis consisting of two components, a femoral component and a tibial plateau, which are mated and operable in conjunction along with the natural members remaining after resection to simulate the natural movement of a knee joint. However, the concepts of the present invention can be applied to other joints as well.

Figure 1:
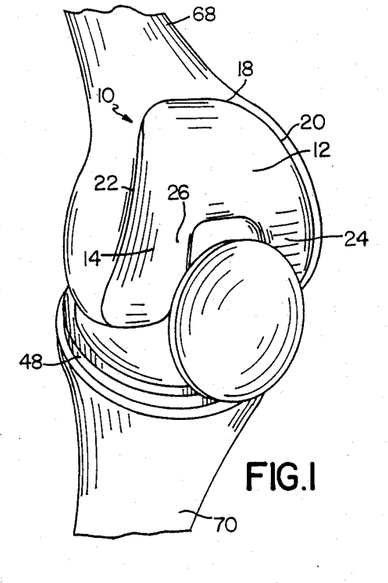
FIGS. 1 and 3 are anterior views of a condylar replacement total knee.
Figure 2:
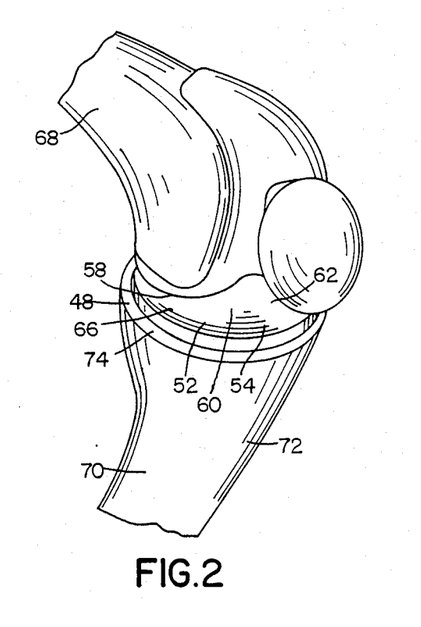
FIG. 2 is a side view of FIG. 1.
Figure 3:
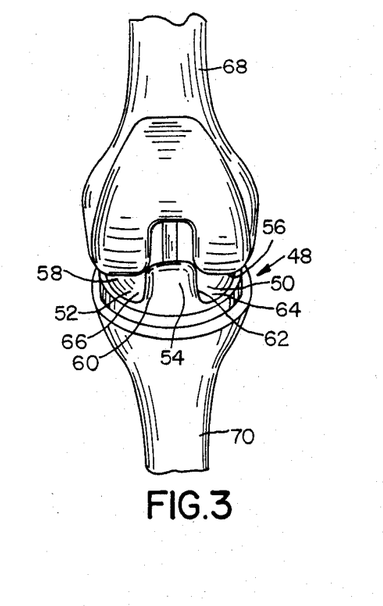

FIGS. 1-3 illustrate the femoral component 10 (referred to as the femoral component) of the present invention. FIG. 1 is an anterior view of a condylar replacement total knee, fitted into a knee joint. FIG. 2 is a side view, and FIG. 3 is an anterior view with the patella removed to show the posterior cruciate liament. The femoral component 10 comprises a lateral condyle 12, medial condyle 14, intramedullary stem 16 (see FIG. 12A), and a trochlear surface 18. As best shown in FIG. 1, the femoral component 10 comprises extension surfaces (lateral) 20 and (medial) 22, as well as flexion surfaces (lateral) 24 and (medial) 26.

Descriptions of femoral geometry have been provided by several authors. See, e.g., Mensch, J. S. et al., "Knee Morphology As A Guide To Knee Replacement", Clin. Orth. No. 112, October 1975, pp. 231-241. Profiles of the femoral condyles in the sagittal plane were shown in 1972 (Seedhom, B. B., et al., "Dimensions of the Knee", Annals of Rheumatic Disease, Vol. 31, pp. 54-58 (1972)), and modelled by various mathematical curves (Langa, G. S., "Experimental Observations and Interpretations on the Relationship Between the Morphology and Function of the Human Knee Joint", Acta Anat., Vol 55, pp. 16-38 (1963); Erkman, M. J. et al., "A Study of Knee Geometry Applied to the Design of Condylar Prosthesis", Biomedical Engineering, Vol. 9, pp. 14-17 (1974); and Rehder, U., "Morphometrical Studies on the Symmetry of the Human Knee Joint: Femoral Condyles", Journal of Biomechanics, Vol. 16, pp. 351-361 (1983)). However, the above data is limited in its ability to describe the three-dimensional geometry of the surfaces. Such description could have application in computer modelling of the knee joint in order to study joint mechanics. Another area of application is in knee prosthesis design and evaluation.

To design the femoral component of one form of the present invention, piecewise mathematical analog of an average anatomical femoral surface geometry was used. The preferred method of calculating the femoral surface comprises the sectioning of embedded cadaver knees into twenty-five sections. The sections were copied and digitized into a computer, using thirty to forty points per section, with a greater point density around the condylar surfaces. A typical set of sections viewed from the anterior and lateral sides are shown in FIGS. 4, 4A and 4B.

Figure 4:
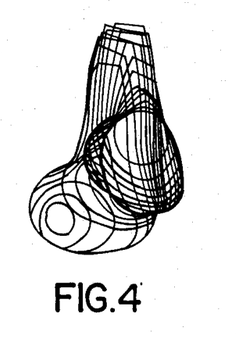
FIGS. 4, 4A, and 4B are computer generated views of a femur.
Figure 4A:
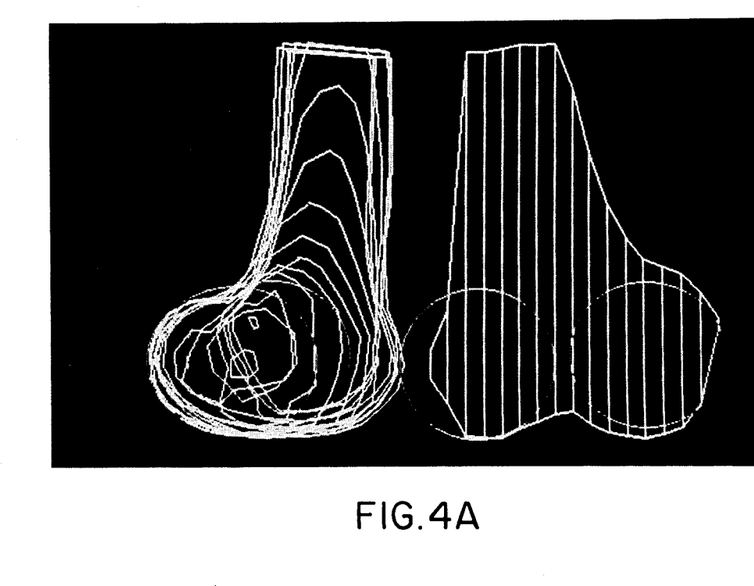
Figure 4B:
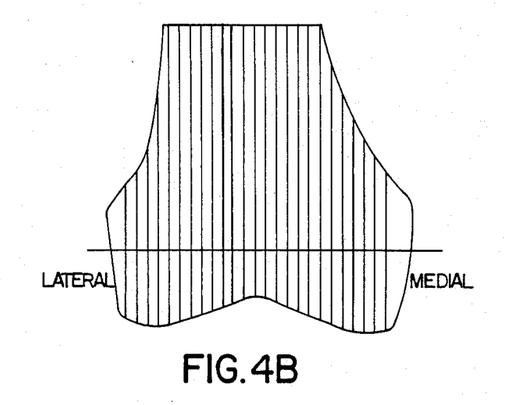

FIG. 4 shows a view of the average femur as seen from the anterior—lateral. In that computer model there are twenty-five parallel sagittal sections, each section having forty points. FIG. 4A shows front and side views (note that front view seen on the right side of FIG. 4A has only seventeen sections), and FIG. 4B shows a sketch of the sections from the front. The information on average profiles and shapes of the bearing surfaces was used to develop geometrical analog. By parametrising the various regions of the bearing surfaces, a computer model was created which is useful for prosthetic design.

Using the computerized average, it was determined that regions along the posterior femoral condyles, critical to the mechanical function of the knee, could best be described as spheroidal sections. Additional geometrical analogs, including toroidal and conical surfaces, were used to describe the bearing surfaces. This led to a mathematical model, an important feature being that the three bearing surfaces, the lateral condyle, the medial condyle, and the patella groove, are each substantially parallel to one another in differing sagittal planes.

The femoral component is preferably constructed of an inert metal alloy—stainless steel, cobalt-chromium alloy, for example, those sold under the trademarks VITALLIUM or ZIMALLOY, or a titanium alloy being suitable and preferred. The component may be formed by molding molten, softened or powdered alloy metal, or by machining or otherwise shaping the metal or other material, e.g., using computer numerical control (CNC). The computer design lends itself to CNC machining of an all plastic knee or of machine molds using CNC from which the knee can be made from injection molding.

Figure 5:
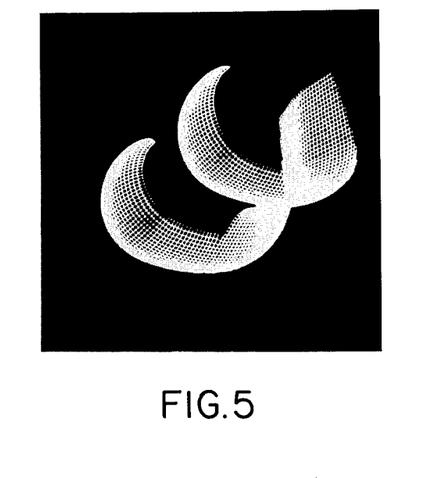
FIG. 5 is a piecemeal mathematical representation of the anatomical femoral surfaces.

FIG. 5 represents a piecewise mathematical representation of the anatomical femoral surfaces. This is the basis for the femoral component surface. The surface is contained in a computer program, which will generate a surface of required size and shape, by expanding, contracting, or distorting the average surface.

Figure 5A:
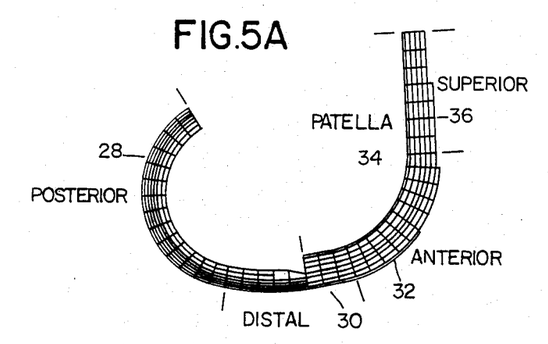
FIGS. 5A-C are geometric analogs of femoral
Figure 5B:
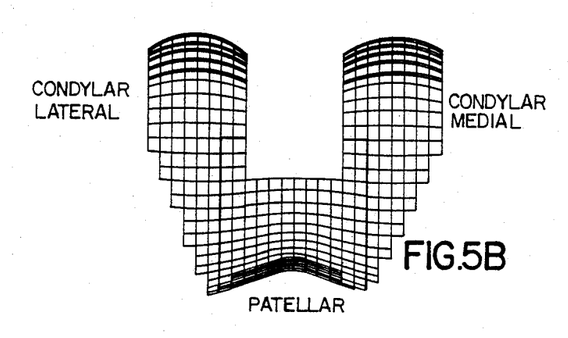
Figure 5C:
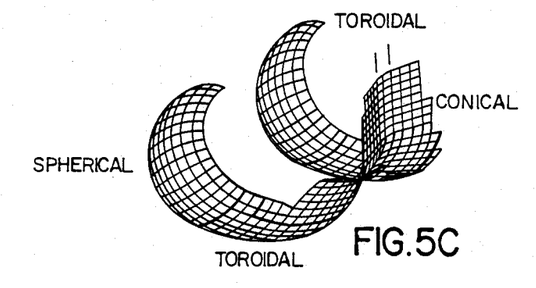
Figure 6:
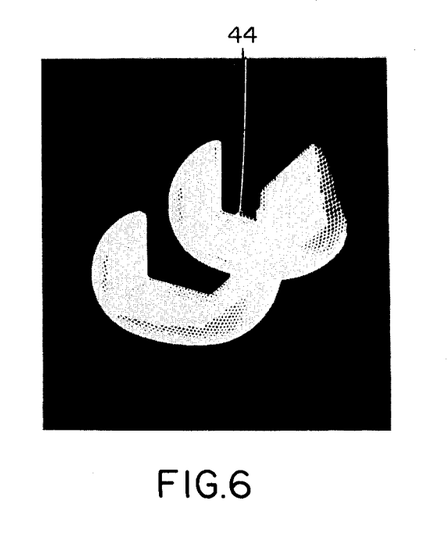
FIG. 6 is a mathematical representation of a complete femoral component.
Figure 7:
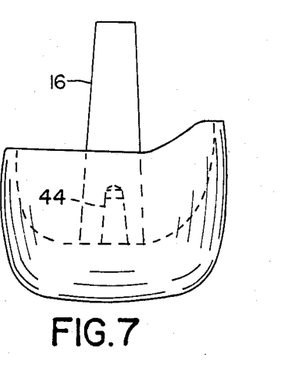
FIG. 7 is a side view of the femoral component showing the femoral peg.
Figure 8:
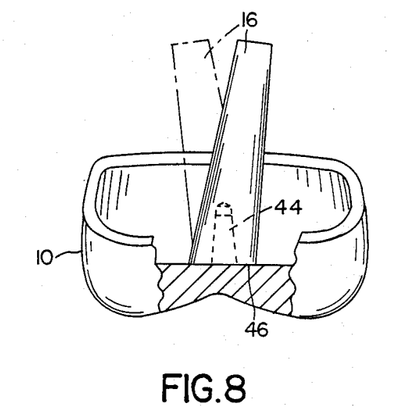
FIG. 8 is a front view of the femoral component showing the long stem in place.

One method contemplated is to take the overall dimensions of a patient's natural joint, and then to distort the average surface which has been stored, in three dimensions so as to approximate the three dimensional size of the patient's joint, and then to make the prosthesis by CNC (computer numerical control) machining techniques to arrive at a prosthesis which will fit in the patient's system precisely as his natural joint, but in which the articulating surfaces will conform operationally to the surfaces generated by the computer synthesis of the average surfaces. Another method is to develop a number of average surfaces covering different size ranges, and then to select the nearest one in size to the joint of the patient. FIG. 5A shows the geometrical analog of femoral condyles, including the posterior 28, distal 30, anterior 32, patella 34, and superior 36 regions. FIG. 5B is a geometrical analog of condylar surfaces showing the lateral condylar, medial condylar, and patellar bearing surfaces 12, 14, 18. FIG. 5C is a third geometric analog of the condylar surfaces showing the spherical, toroidal, and conical surface analogs, referred to by reference numerals 38, 40, and 42, respectively.

The tibial plateau component 48 of the present invention is also shown in FIGS. 1-3. The tibial plateau 48 includes lateral articular surface 50, medial articular surface 52, and therebetween raised surface 54. As used herein, "articular surface" refers to the part of the surface of a component of the prosthesis which during normal joint movement is in pressure receiving relation (either by direct contact or by near contact with a lubricating medium therebetween) with another component. Thus in the case of the tibial plateau 48, its articular surfaces 50, 52 are those portions which contact (usually with a fluid film therebetween) the femoral component. Articular surfaces 50, 52 include upwardly raised guiding-bearing lateral surfaces 56, and upwardly raised guiding-bearing medial surfaces 58. Within guiding-bearing surfaces 56 and 58 are extension surfaces 60 and 62. Between guiding-bearing surfaces 56 and 58 and extension surfaces 60 and 62, respectively, are flexion surfaces (lateral) 64 or (medial) 66. The flexion, extension, and guiding surfaces 56-66 overlap and coincide at certain points.

Preferably, the tibial plateau is constructed of an inert molded, high density plastic, such as high density polyethylene. The CNC machining advantages discussed above with respect to the femoral component also apply to the manufacture of the tibial plateau component 48.

Tibial plateau 48 and femoral component 10 are shown together in a flexion position in FIG. 2. In this view, the leg bones, namely the femur 68, the tibia 70, and the fibula 72, are also shown. The cement, e.g., methyl methacrylate 74, used to seat the tibial plateau 48, is also shown. Femoral component 10 contacts the flexion surfaces 64, 66 of the tibial plateau 48 at two or more lateral-medial spaced substantial points, which lend stability to the joint during flexion. FIG. 3 illustrates the two components in the position of extension, in which position three or more lateral, medial, and anterior-posterior spaced substantial points of contact exist between the opposed surfaces, whereby the joint is effectively locked in extension.

The term "substantial points of contact" are used herein to describe the contact betweeen two mating curved surfaces, the male member of which is slightly smaller in curvature. In theory a point or line contact is made, but in practice, when at least one member is resilient, more than a point or line of contact results under pressure.

With the exception of the design of the femoral component, as decribed above, and the details set forth hereinbelow, the prosthesis of the present invention is similar to the Ewald prosthesis described in U.S. Pat. No. 3,798,679, the disclosure of which is hereby incorporated herein by reference.

An important distinction and advancement over the prior art is the incorporation of laxity concepts within the design parameters of the tibial plateau. Laxity is generally defined as the partially restrained motion or free play of a joint in a specified direction, before substantial ligamentous restraint takes place at the extremes of motion. Laxity can include linear or rotational translation in any of the three mutually perpendicular coordinate axes. For purposes of the present invention, laxity is only considered in anterior-posterior displacement, medial-lateral displacement, and internal-external rotation, these being the most significant.

The term "total laxity" is the total amount of laxity movement or rotation which occurs between the limits of the applied force or torque. In the natural joint, the limits of laxity are determined by the interaction of the menisci, the ligaments, the femoral component, and the tibial plateau. However, in a prostheses, the menisci and several ligaments are removed, and the limits of laxity are determined by the natural components remaining after resection acting cooperatively with forces introduced by the contour of the prosthetic interface and the user's weight.

Figure 11A:
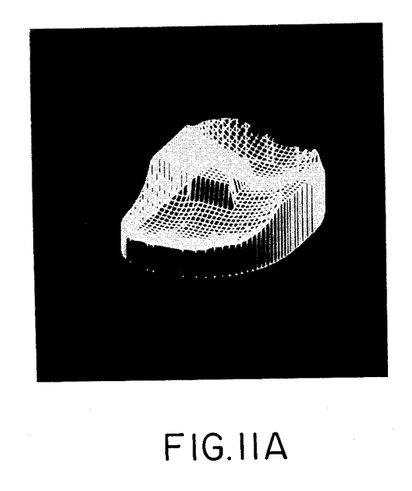
FIG. 11A is a tibial surface generated by sweeping the femoral component through an average knee motion path.

A simple tibial surface can be generated by the above-mentioned femoral surface by simply moving the femoral surface about a fixed axis, producing a cylindrical type of surface. However, to produce a surface which incorporates features of anatomical knee motion, laxity characteristics, and stability, the tibial plateau of the prosthesis must be contoured in an non-anatomical way. Therefore, in accordance with the present invention, the tibial plateau can be designed in different ways, for example by incorporating the average three-dimensional femoral motions along each of the three coordinate axes, plus internal-external rotation and anterior-posterior displacement. The 3-dimensional motion of the femur on the tibia is mathematically described by using data of anatomical knee motion such as published by Kurosawa, et al (Kurosawa, H.; Walker, P. S.; Abe, S.; Garg, A.; Hunter, T.; Journal of Biomechanics, 18:487–499, 1985). The mathematical equations enable the femur to be positioned correctly on the tibia as a function of knee flexion angle. A tibial surface generated by sweeping the aforementioned femoral surface through an anatomical knee motion path is shown in FIG. 11A.

Figure 11B:
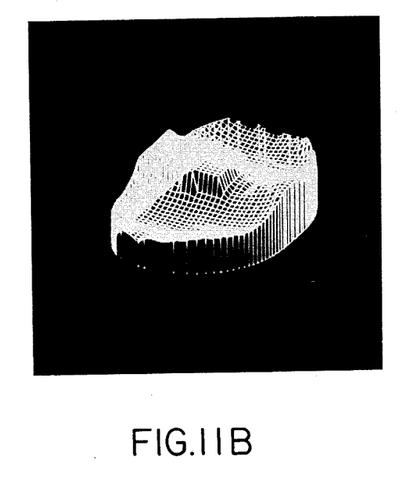
FIG. 11B is a computer generated series of curves representing laxity motion of a knee.
Figure 11C:
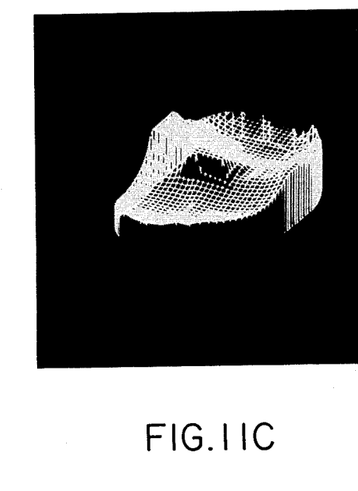
FIG. 11C is a computer generated superimposition of the laxity curves of FIG. 11B onto the average knee motion of FIG. 11A.

Next, laxity, otherwise thought of as flexibility of the knee, was considered. The laxity behaviour for the anatomical knee has been reported by several authors including Markolf, et al (Markolf, K. L.; Bargar, W. L.; Shoemaker, S. C.; Amstutz, H. C.; Journal of Bone & Joint Surgery, 63-A:570–585, 1981). The laxity curves show that the resistance to displacement from the neutral position, steadily increase with the displacement, the more so when the knee is weight-bearing. Cubic equations to express this laxity behaviour were determined, and then the theory of Walker (Walker, P. S.; Ch. 4, p. 202-204, Human Joints & Their Artificial Replacements, publ. C. C. Thomas, Springfield, Ill., 1977) was used to express this in terms of horizontal, rotational and vertical movements of the femur on the tibia. A tibial surface generated by sweeping the femoral surface through laxity curves at different flexion angles is shown in FIG. 11B Different motions can be superimposed, for example average knee motion and average laxity, as shown in FIG. 11C. The tibial surfaces of the present invention differ from hitherto known prostheses, because they have built into them surface geometries which produce precise and mathematically defined motion, laxity, and stability. These tibial surfaces do not have simple geometries which can be defined by simple radii, but have continuously changing radii all over the surface. These surfaces of the present invention differ additionally from hitherto known prostheses. These surfaces of the present invention, especially when they include characteristics of normal knee motion such as rollback, are especially advantageous. Motion along different paths will be smooth with no sudden stops in any direction but gradually increasing resistance. Such surfaces will readily accomodate different motion paths for different activities and individuals, and will allow a degree of latitude in surgical placement.

Further, the addition of laxity parameters as specifically defined above, provides provide a narrow gap between the femoral component and the tibial plateau laterally of the primary articular surface. This is advantageous because it facilitates access to the articular surface of the synovial fluid around the prosthesis, and also enables debris to be removed, thereby improving the life and operation of the prosthesis.

Figure 9:
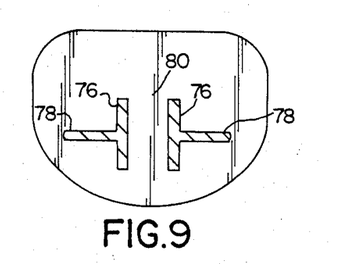
FIG. 9 is a bottom view of the tibial component.
Figure 10:
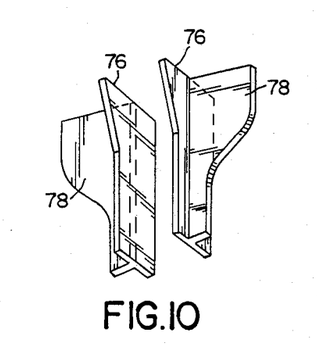
FIG. 10 is a perspective view of the tibial blades.

The tibial plateau can be similarly made more versatile by replacing the conventional stem blade with a design shown in FIGS. 9-10. The stem blades of the present invention comprise transverse blades 76 and 78. A specially deigned gap 80 between blades 76 allow a longer stem to be press fit within, for situations calling for a long stem. FIG. 9 shows a bottom view of the tibial component 48. The location of the blade fixation is shown located anteriorly so as to be in line with the canal of the bone. Thus, when a long stem is added, it goes directly down the canal.

FIG. 10 is a perspective view of the tibial blades. This provides fixation for standard components, and gives resistance to shear forces and bending moments in all planes. For added fixation, a long stem is pressed into the space 80 between the blades.

Figure 13:
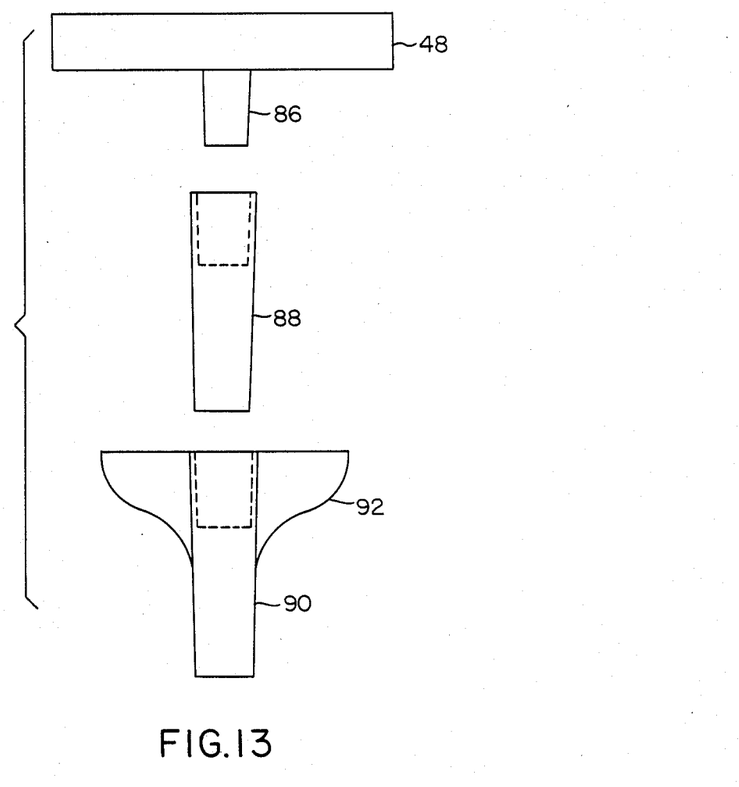
FIG. 13 illustrates an alternative means of stabilizing the tibial plateau in accordance with the present invention.

FIG. 13 is another embodiment of the tibial fixation means. Instead of using the arrangement shown in FIGS. 9 and 10, a tapered peg 86 can be attached to the base of the tibial component 48. Onto peg 86 can be cemented a longer stem 88 or a stem 90 having blades 92 extending therefrom. Such an arrangement provides added flexibility in case of bone loss or other situations.

Figure 12A:
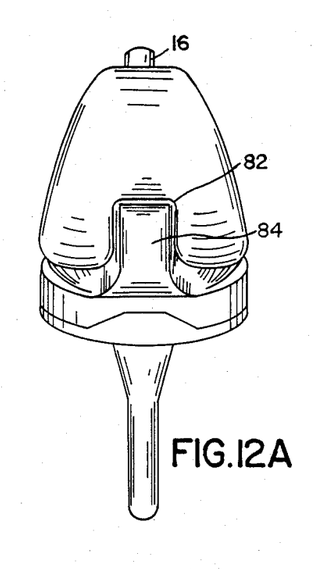
FIGS. 12A and B illustrate a stabilized version of the present invention.
Figure 12B:
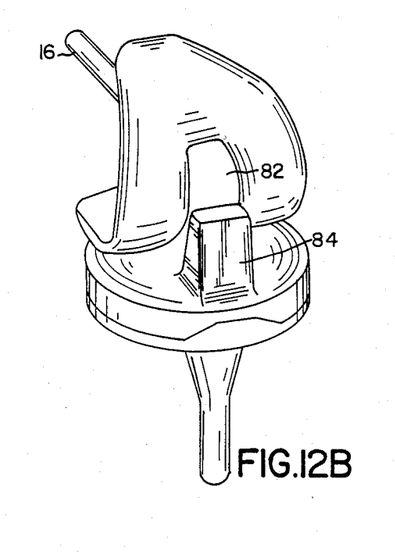

FIGS. 12A and B illustrate a stabilized version of the standard condylar knee. The femoral component has an intercondylar box 82 which receives a raised part or post 84 of the tibial component. If the post 84 is about half the height shown, then anterior-posterior stability is obtained. This substitutes for the anterior and posterior cruciate ligaments. If the post is about the height shown, varus- valgus stability is also obtained, substituting for the lateral and medial collateral ligaments.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What we claim is:

1. A method of making a prosthesis for the replacement of the male and female articular surfaces of a human joint having a male articular surface bearing portion and a female articular surface bearing portion respectively adapted to be affixed to the anatomical bone structure adjacent said joint subsequent to the surgical resection of said bone structure for the removal of the anatomical male and female articular surfaces thereof such that the male and female articular surfaces of said prosthesis are disposed in pressure receiving relation to each other and adapted for articulating movement through a path between extreme positions of extension and flexion, said method comprising:

generating and storing in a computer a mathematical model of a male articular surface contour, said model contour representing an average of a preselected number of actual anatomical male articular surface contours of said joint derived from mathematical analogues of empirical measurements of the anatomical surface geometries of said preselected number of actual anatomical male articular surface contours;

generating a first set of computer numerical control signals corresponding to said model male articular surface contour;

machining said model male articular surface contour onto a first workpiece in direct response to said first set of computer numerical control signals;

forming said male articular surface bearing portion of said prosthesis utilizing said first machined workpiece;

generating and storing in a computer a model female articular surface contour for receiving said model male articular surface contour in articulating relation, said model female articular surface contour corresponding to the surface described by sweeping said model male articular surface contour through the average motion path of said joint;

superimposing laxity parameters upon said model female articular surface contour in said computer to account for the partially restrained motion in a specified direction before substantial ligamentious restraint takes place at the extremes of motion in a normal anatomical human joint of the type to be replaced by the prosthesis, thereby creating a resultant model female articular surface contour in said computer;

generating a second set of computer numerical control signals corresponding to said resultant model female articular surface contour;

machining said resultant female articular surface onto a second workpiece in direct response to said second set of computer numerical control signals; and forming said female articular surface bearing portion of said prosthesis utilizing said second machined workpiece.

2. The method of claim 1 further characterized by further machining the first and second machined workpieces respectively to form the male and female articular surface bearing portions of said prosthesis respectively.

3. The method of claim 1 wherein the first and second machined workpieces respectively comprise the male and female articular surface defining walls of the cavity portion of molds adapted for the molding of the male and female articular surface bearing portions of said prosthesis respectively.

* * * * *